(12) United States Patent
Barrus (10) Patent No.: US 9,795,413 B2
(45) Date of Patent: Oct. 24, 2017

(54) SPINAL FIXATION MEMBER (71) Applicant: K2M, Inc., Leesburg, VA (US)

(72) Inventor: Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/927,574

(22) Filed: Oct. 30, 2015

(65) Prior Publication Data

US 2016/0120575 A1     May 5, 2016

Related U.S. Application Data

(60) Provisional application No. 62/072,541, filed on Oct. 30, 2014.

(51) Int. Cl.
    *A61B 17/70*     (2006.01)
    *A61B 17/56*     (2006.01)
    *A61B 17/68*     (2006.01)

(52) U.S. Cl.
    CPC .......... *A61B 17/702* (2013.01); *A61B 17/701* (2013.01); *A61B 17/7004* (2013.01); *A61B 17/7025* (2013.01); *A61B 17/7031* (2013.01); *A61B 2017/564* (2013.01); *A61B 2017/681* (2013.01)

(58) Field of Classification Search
    CPC . A61B 17/7004; A61B 17/701; A61B 17/702; A61B 17/7031; A61B 17/7025; A61B 17/7001; A61B 17/7037; A61B 17/7022; A61B 17/7067; A61B 17/7053; A61B 17/863; A61B 2017/681; A61B 2017/564
    USPC ....................... 606/246–279, 86 A
    See application file for complete search history.

(56) References Cited

U.S. PATENT DOCUMENTS

| | | |
|---|---|---|
| 5,658,286 A | 8/1997 | Sava |
| 6,102,912 A | 8/2000 | Cazin et al. |
| 7,520,879 B2 | 4/2009 | Justis et al. |
| 7,563,274 B2 | 7/2009 | Justis et al. |
| 7,588,575 B2 | 9/2009 | Colleran et al. |

(Continued)

FOREIGN PATENT DOCUMENTS

WO     2011/066231 A1     6/2011

OTHER PUBLICATIONS

European Search Report for EP 15 19 2440 dated Mar. 21, 2016.

*Primary Examiner* — Pedro Philogene
(74) *Attorney, Agent, or Firm* — Carter, DeLuca, Farrell & Schmidt, LLP (57) ABSTRACT

A system for fixing spinal vertebrae utilizes a spinal rod that has varying properties along its length such that a lower stiffness portion is placed in the cranial or caudal end positions of the spinal rod to address potential adjacent level failure. The spinal rod includes a core member formed of a first material having a first modulus of elasticity and a sheath member formed of a second material having a second modulus of elasticity different from the first modulus of elasticity. The core member includes a first portion having a uniform outer diameter and a second portion extending from the first portion. At least a portion of the second portion has an outer diameter smaller than the uniform outer diameter of the first portion. The sheath member has a lumen extending therethrough that is sized for slidably receiving the second portion of the core member therein.

18 Claims, 5 Drawing Sheets

(56) References Cited

U.S. PATENT DOCUMENTS

| | | | |
|---|---|---|---|
| 7,604,653 B2 | 10/2009 | Kitchen | |
| 7,618,442 B2 | 11/2009 | Spitler et al. | |
| 7,766,942 B2 | 8/2010 | Patterson et al. | |
| 7,931,676 B2 | 4/2011 | Veldman et al. | |
| 2005/0065515 A1 | 3/2005 | Jahng | |
| 2007/0191841 A1 | 8/2007 | Justis et al. | |
| 2008/0086130 A1 | 4/2008 | Lake et al. | |
| 2008/0177388 A1* | 7/2008 | Patterson | A61B 17/705 623/17.16 |
| 2008/0300633 A1* | 12/2008 | Jackson | A61B 17/702 606/257 |
| 2009/0259257 A1* | 10/2009 | Prevost | A61B 17/702 606/255 |
| 2011/0071570 A1* | 3/2011 | Trieu | A61B 17/7011 606/254 |
| 2012/0029564 A1 | 2/2012 | Trieu et al. | |
| 2013/0144342 A1* | 6/2013 | Strauss | A61B 17/701 606/261 |
| 2015/0157363 A1* | 6/2015 | Noordeen | A61B 17/7032 606/261 |

* cited by examiner

SPINAL FIXATION MEMBER

CROSS-REFERENCE TO RELATED APPLICATIONS

This application claims the benefit of, and priority to, U.S. Provisional Patent Application Ser. No. 62/072,541, which was filed on Oct. 30, 2014, the entire contents of which are hereby incorporated herein by reference.

TECHNICAL FIELD

The present disclosure relates generally to a spinal fixation member, and more particularly, to devices, systems, and surgical methods for securing a spinal fixation member during orthopedic spine surgery.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between the vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal fixation apparatus are widely employed in surgical processes for correcting spinal injuries and diseases. When the disc has degenerated to the point of requiring removal, there are a variety of interbody implants that are utilized to take the place of the disc. These include interbody spacers, metal cages, and cadaver and human bone implants. In order to facilitate stabilizing the spine and keeping the interbody in position, other implants are commonly employed, such as bone screws and rods. Depending on the pathology and treatment, a surgeon will select the appropriate spinal rod material and size, specifically, the cross-sectional diameter of the spinal rod.

One growing trend seen post surgical treatment of a patient's spine is the incidence of proximal junctional kyphosis (PJK), which is typically an adult spinal deformity surgical outcome if the lumbar lordosis and thoracic kyphosis are not properly restored post surgery. PJK appears at or above the cranial-most thoracic level treated. Even though PJK most commonly occurs in the thoracic region of the spine, it can also occur in various spinal regions and may occur above or below the instrument levels and may impact the next adjacent level or two that is not instrumented. This type of failure is called adjacent level failure. Symptoms of PJK and adjacent level failure include pain, neurological deficit, ambulatory difficulty, and poor maintenance of sagittal balance. For patients that demonstrate these symptoms, often the only treatment is an additional surgery. The incidence rate of PJK may be upward of 50% of long construct, instrumented fusion cases. Factors contributing to this condition are the end vertebrae selection, facet violation, weakened structural support due to significant soft tissue disruption, extensive junctional paraspinal musculature dissection, and loss of integrity of the posterior tension band.

One thought to address the problem of PJK, which is caused by the accelerated degeneration of the joint capsules and smaller articular processes at one or two levels above or below the junctional region, is to decrease the structural rigidity of the construct at the top of the construct just below the proximal junction, thereby providing a transition from the relatively stiff instrumented spine to the more flexible, non-instrumented spine to minimize facet capsule and muscle disruption.

Spinal rods are typically made of cobalt chrome, stainless steel, or titanium alloy. However, in order to transition to a less stiff construct at the top, other less rigid materials and shapes may be employed to provide the desired stiffness.

One design for a spinal rod is shown and described in US Patent Appl. Pub. No. 2013/0144342 entitled "Spine Stabilization System," the entire contents of which are hereby incorporated herein as if repeated in their entirety. The present disclosure relates to an improved rod of the type disclosed in the foregoing US published application, providing, for example, a rod of the type shown and described in the US published application, 2013/0144342, to be fabricated from titanium or titanium alloy with favorable stiffness or rigidity characteristics.

A continuing need exists for an improved device, an improved system, and an improved method for performing spine surgery that does not create additional morbidity post surgical treatment.

SUMMARY

The present disclosure is directed to fixing spinal vertebrae with a spinal fixation member or spinal rod having varying stiffness properties along its length. The spinal fixation member may constitute various materials or material combinations, as well as various shapes, to provide the desired stiffness properties.

In accordance with an aspect of the present disclosure, a spinal rod for aligning vertebral bodies includes a core member formed of a first material having a first modulus of elasticity and a sheath member formed of a second material having a second modulus of elasticity different from the first modulus of elasticity. The core member includes a first portion having a uniform outer diameter and a second portion extending from the first portion. At least a portion of the second portion has an outer diameter smaller than the uniform outer diameter of the first portion. The sheath member has a lumen extending therethrough that is sized for slidably receiving the second portion of the core member therein.

The first portion of the core member may be cylindrical and have a circular cross-section and/or the second portion of the core member may be tapered. The first and second portions of the core member may be of equal lengths.

In embodiments, the sheath member has an outer diameter that matches the uniform outer diameter of the first portion of the core member. In some embodiments, the sheath member has a compound shape. In certain embodiments, the sheath member includes an elongated body portion, an elongated head portion, and an elongated neck portion interconnecting the elongated body portion and the elongated head portion. The elongated body portion may have an outer diameter that matches the uniform outer diameter of the first portion of the core member.

The first modulus of elasticity may be higher than the second modulus of elasticity. In embodiments, the core member is fabricated from a biocompatible metallic material and/or the sheath member is fabricated from a biocompatible polymeric material.

The core member may include a third portion extending from the first portion, with at least a portion of the third portion having an outer diameter that is smaller than the uniform outer diameter of the first portion. The spinal rod may include a second sheath member having a lumen extending therethrough that is sized for slidably receiving the third portion of the core member therein. The second sheath member may be formed of a third material having a third modulus of elasticity different from the first modulus of elasticity.

In accordance with another aspect of the present disclosure, a kit for spinal surgery includes: a core member having a first portion and a second portion, the first portion having a first outer diameter, and the second portion having a second outer diameter less than the first outer diameter; a first sheath member having a first lumen for slidably engaging the second portion of the core member; and a second sheath member having a second lumen for slidably engaging the second portion of the core member, wherein one of the first or second sheath members has an asymmetrical cross-sectional profile. The core member may have a third portion opposite the second portion, and the third portion may have a third outer diameter less than the first outer diameter.

In accordance with yet another aspect of the present disclosure, a method for aligning vertebral bodies includes: inserting a first portion of a core member of a spinal rod into a first pedicle screw secured to a first vertebral body, the first portion of the core member having a uniform outer diameter, and the core member being formed of a first material having a first modulus of elasticity; and inserting a sheath member having a second portion of the core member disposed within a lumen of the sheath member into a second pedicle screw secured to a second vertebral body, at least a portion of the second portion of the core member having an outer diameter smaller than the uniform outer diameter of the first portion of the core member, and the sheath member being formed of a second material having a second modulus of elasticity different from the first modulus of elasticity.

The method may further include anchoring the first and second pedicle screws into the first and second vertebral bodies prior to inserting the first portion of the core member into the first pedicle screw and inserting the sheath member into the second pedicle screw. In some embodiments, the first vertebral body is situated caudal to the second vertebral body, and inserting a first portion of the core member into the first pedicle screw includes positioning the first portion of the core member in a caudal orientation relative to the second portion of the core member. In some other embodiments, the first vertebral body is situated cranial to the second vertebral body, and inserting a first portion of the core member into the first pedicle screw includes positioning the first portion of the core member in a cranial orientation relative to the second end portion of the core member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor (e.g., a surgeon), a nurse, or any other care provider, and may include support personnel. Throughout this description, the term "proximal" will refer to a portion of a device or component thereof that is closer to a clinician, and the term "distal" will refer to the portion of the device or component thereof that is farther from the clinician. "Cranial" refers to a spine segment closer to the head of a patient, whereas "caudal" refers to the spine segment closer to the feet of the patient. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figures 1, 2:
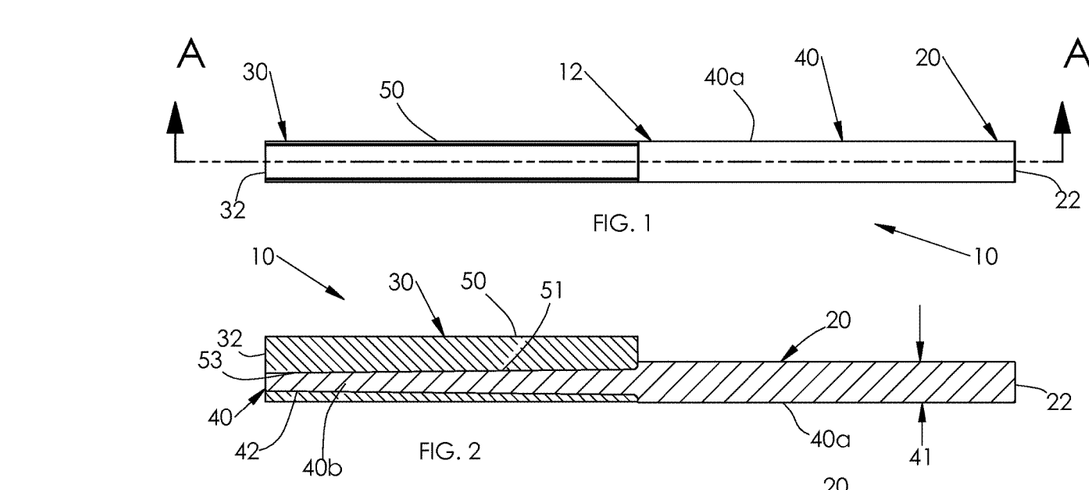
FIG. 1 is a top view of a spinal fixation member in accordance with an embodiment of the present disclosure.
FIG. 2 is a cross-sectional view of the spinal fixation member of FIG. 1, taken along line A-A of FIG. 1.
Figure 3:
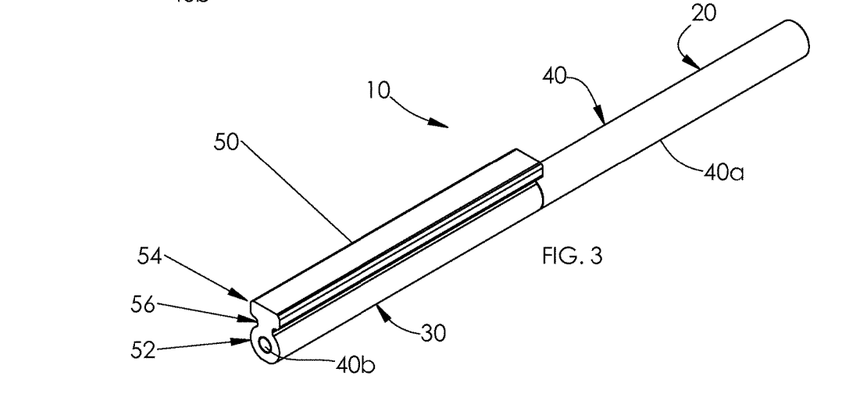
FIG. 3 is an isometric perspective view of the spinal fixation member of FIG. 1.

Referring now to FIGS. 1-3, a spinal fixation member or spinal rod 10 is defined by an elongated body 12 having a first end portion 20 and a second end portion 30 terminating at outermost ends 22 and 32, respectively. A core member 40 extends along the entire length of the elongated body 12 (see e.g., FIG. 2), and includes a first portion 40a and a second portion 40b. The length of the first and second portions 40a and 40b of the core member 40 coincide with the length of the first and second end portions 20 and 30, respectively, of the spinal fixation member 10. The first end portion 20 of the spinal fixation member 10 includes only the first portion 40a of the core member 40, and the second end portion 30 of the spinal fixation member 10 includes the second portion 40b of the core member 40 and an outer sheath member 50. While the first and second end portions 20 and 30 of the spinal fixation member 10 are each shown as extending along about half or equal lengths of the elongated body 12 of the spinal fixation member 10, it should be understood that the length of the first end portion 20 may be shorter or longer than the length of the second end portion 30 depending on the desired properties (e.g., stiffness, length, etc.) of the spinal fixation member 10.

At the first end portion 20 of the spinal fixation member 10, the first portion 40a of the core member 40 is cylindrical, having a substantially circular cross-section and a uniform outer diameter 41 (FIG. 2) along the length of the first end portion 20. It should be understood, however, that the first portion 40a of the core member 40 may be any shape having a uniform outer dimension, such as tubular, ovular, elliptical, or rectangular, for example, among other shapes, such as compound shapes, including shapes having symmetrical and asymmetrical cross-sectional profiles.

As shown in FIG. 2, at the second end portion 30 of the spinal fixation member 10, the second portion 40b of the core member 40 is stepped or tapered along at least a portion of the length thereof, and is defined as an inner member disposed within the outer sheath member 50. The outer diameter of the second portion 40b of the core member 40 varies along at least a portion of the second portion 40b and is smaller than the fixed outer diameter 41 of the first portion 40a of the core member 40. The second portion 40b of the core member 40 can have a continuous tapering profile extending towards the outermost end 32 of the spinal fixation member 10, or can include one or more tapered segments each having a different taper angle or dimension (e.g., stepped regions).

With reference to FIGS. 2 and 3, the outer sheath member 50 is disposed over the second portion 40b of the core member 40 and includes an inner surface 51 defining a lumen 53 that is complementary in geometry with an outer surface 42 of the second portion 40b of the core member 40. The outer sheath member 50 may slidably engage the second portion 40b of the core member 40, which would allow for loading and compression of the associated vertebral bodies and discs, or may be fixedly secured to the second portion 40b of the core member 40. The outer sheath member 50 may be retained on, or affixed to, the second portion 40b of the core member 40, for example, by adhesion, overmolding, riveting, pinning, interference fit, press fit, among other securing means within the purview of those skilled in the art. The outer sheath member 50 is dimensioned to extend along the entire length of the second portion 40b of the core member 40, with one end abutting an end of the first portion 40a of the core member 40 and one end aligned with the outermost end 32 of the spinal fixation member 10. It is envisioned, however, that the outer sheath member 50 may be longer or shorter than the second portion 40b of the core member 40 depending on the stiffness properties desired for the spinal fixation member 10.

As shown in FIG. 3, the outer sheath member 50 has a compound shape. The compound shape includes an elongated body portion 52, an elongated head portion 54, and an elongated neck portion 56 connecting the body portion 52 with the head portion 54. The body portion 52 of the outer sheath member 50 is shaped substantially identically as the first portion 40a of the core member 40 such that the body portion 52 of the outer sheath member 50 is shaped to match the outer diameter 41 (FIG. 2) of the first portion 40a of the core member 40. As shown, and described above, the first portion 40a of the core member 40 is cylindrical in shape, and accordingly, the body portion 52 of the outer sheath 50 is also cylindrical so that the spinal fixation member 10 has a substantially uniform diameter along the length of the elongated body 12. The neck portion 56 extends from the body portion 52 and transitions to the head portion 54 which, in the present embodiment, is a rectangular top section. It should be understood that the outer sheath member 50 may be any shape that is the same as, or different from, that of the first portion 40a of the core member 40.

The core member 40 may be formed or machined from a biocompatible metallic material such as, but not limited, to titanium alloy, stainless steel, and cobalt chrome. The outer sheath member 50 may be made from a polymeric material including, for example, polyetheretherketone, polyetherimide, polysulfone, polyacetal, polycarbonate, polyurethane, and nylon, and may be formed by injection molding, extruding, compression molding, overmolding, machining or other known methods for shaping polymeric materials as within the purview of those skilled in the art. Accordingly, the core member 40 is formed from a material having a higher modulus of elasticity than the material of the outer sheath member 50, and thus the outer sheath member 50 is formed of a less stiff material than that of the core member 40.

The core member 40 may have a modulus of elasticity of about 75 GPa to about 220 GPa. In embodiments, the core member 40 is formed from a titanium alloy, such as Ti-6A1-4V, having a modulus of elasticity of about 115 GPa. In some embodiments, the core member is formed of stainless steel having a modulus of elasticity of about 190 GPa to about 200 GPa, such as stainless steel 304 or 316. In some other embodiments, the core member 40 is formed from cobalt chrome having a modulus of elasticity of about 220 GPa. The outer sheath member 50 may be formed from a polymeric material having a modulus of elasticity of about 0.3 N/m$^2$ to about 35 N/m$^2$. In embodiments, the core member 40 may be formed from a polymeric material having a modulus of elasticity greater than the modulus of elasticity of the outer sheath member 50, such as polyetheretherketone, which may have a modulus of elasticity of about 2 Gpa. Persons skilled in the art will understand that the materials and configurations of the core member 40 and the outer sheath member 50 may be selected to achieve a desired combination of aggregate properties.

Additionally, the stiffness of the material of the core member 40 at the second portion 40b of the core member 40 may be less than that of the first portion 40a of the core member 40, which has the larger diameter, and the tapering profile of the second portion 40b of the core member 40 may provide a varying stiffness along the length of the second portion 40b of the core member 40. Thus, the combination of, for example, size, shape, and material selection of the core member 40 and the outer sheath member 50, as well as the tapering profile of the second portion 40b of the core member 40, provides the spinal fixation member 10 with a desired stiffness profile along the length of the elongated body 12 of the spinal fixation member 10. Specifically, the outer sheath member 50 may be made of various less stiff materials than the core member 40 so as to provide an overall lower stiffness at the second end portion 30 of the spinal fixation member 10.

Figure 4:
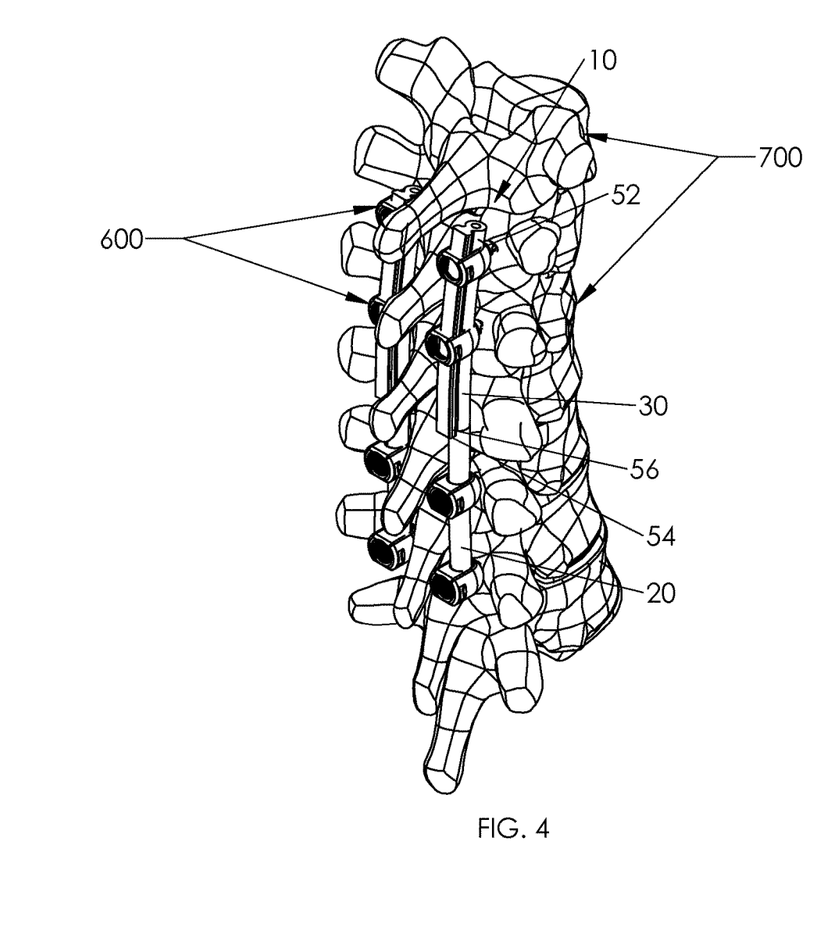
FIG. 4 is an in situ view of the spinal fixation member of FIG. 1.

FIG. 4 shows an in situ view of the spinal fixation member 10, whereby the spinal fixation member 10 is attached to pedicle screws 600. The pedicle screws 600 are anchored into vertebral bodies 700 of a spine. The spinal fixation member 10 is attached to the pedicle screws 600 such that the first and second end portions 20 and 30 are each positioned in respective pedicle screws 600. Pedicle screws 600 may be positioned at any desired position along the spinal fixation member 10. The second end portion 30 of the spinal fixation member 10 may be secured to the pedicle screws 600, such that the neck portion 56 and the head portion 54 of the outer sheath member 50 are disposed at the top of the pedicle screw 600 and do not interfere with the interaction between the body portion 52 of the outer sheath member 50 and the pedicle screw 600. The second end portion 30 of spinal fixation member 10 has a reduced stiffness compared to the first end portion 20. It should be understood that the spinal fixation member 10 can be rotated 180 degrees prior to attachment to the pedicle screws 600, depending on the stiffness levels desired at the cranial and caudal ends of the spinal fixation member 10.

The outer sheath member 50 provides the spinal fixation member 10 with a less stiff second end portion 30 which can be oriented in a cranial orientation to facilitate reducing the stress impact on the cranial, non-instrumented adjacent level to the spinal fixation member 10. Conversely, should less stiffness be desired at the caudal level, the spinal fixation member 10 could be turned 180 degrees to allow the less stiff second end portion 30 of the spinal fixation member 10 to be located in a caudal orientation. Should less stiffness be desired at both the cranial and caudal ends (i.e., a stiffer or more rigid central portion), a sheath and core configuration may be formed on both ends of the spinal fixation member, while the middle portion of the spinal fixation member is a solid and/or stiffer portion than the ends.

Figure 5:
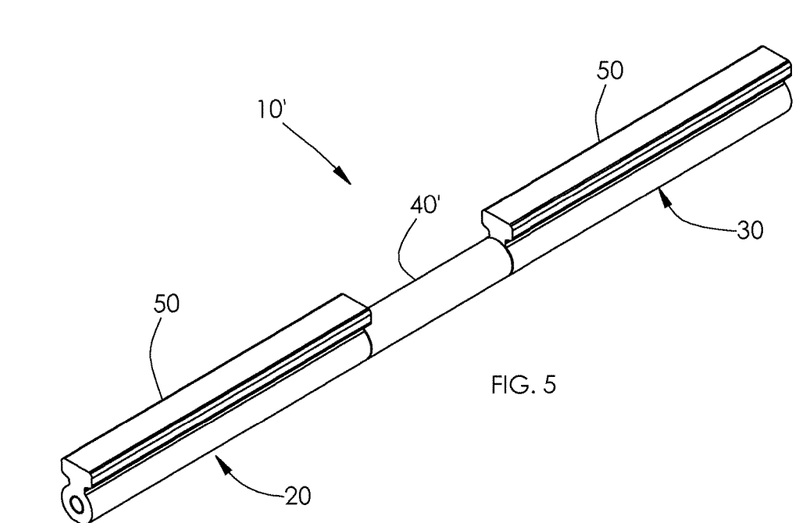
FIG. 5 is an isometric perspective view of a spinal fixation member in accordance with another embodiment of the present disclosure.
Figure 6:
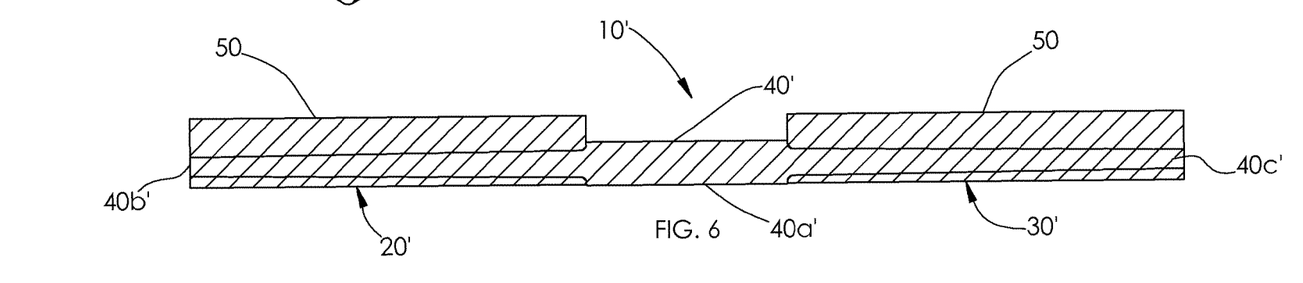
FIG. 6 is a side cross-sectional view of the spinal fixation member of FIG. 5.

Accordingly, in some embodiments, both the cranial and caudal end portions of a spinal fixation member may include an outer sheath member to reduce the stiffness of the spinal fixation member at both the cranial and caudal end portions should a clinician want to address adjacent level failure at both ends of the construct. For example, as shown in FIGS. 5 and 6, a spinal fixation member 10' includes a core member 40' including a first portion 40a' disposed in a middle or central portion of the spinal fixation member 10', and second and third portions 40b' and 40c' that extend from the first portion 40a' towards first and second end portions 20' and 30' of the spinal fixation member 10'. Each of the second and third portions 40b' and 40c' of the core member 40' includes an outer sheath member 50 to reduce the stiffness of the spinal fixation member 10' at both ends of the spinal fixation member 10'. The tapering profile of the second and third portions 40b' and 40c' of the core member 40' may be the same or different, and the outer sheath members 50 disposed over the second and third portions 40b' and 40c' of the core member 40' may be the same or different (e.g., in shape, material, modulus of elasticity, etc.) depending on the desired stiffness profile along the length of the spinal fixation member 10.

Figure 7:
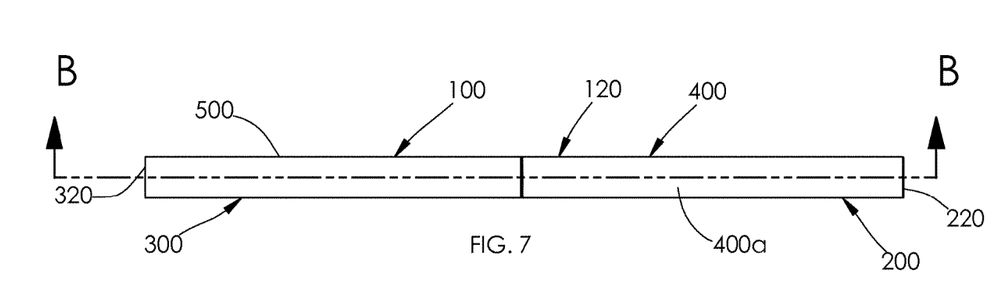
FIG. 7 is a top view of a spinal fixation member in accordance with yet another embodiment of the present disclosure.
Figure 8:
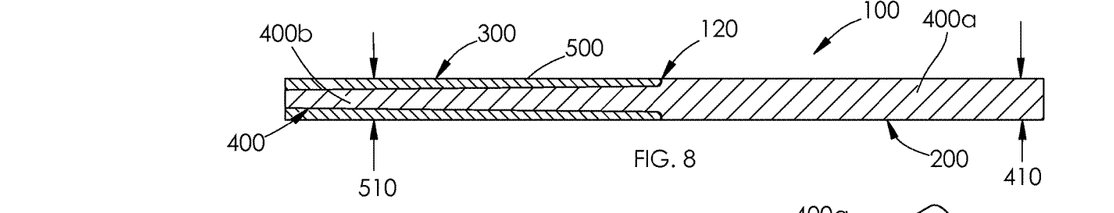
FIG. 8 is a cross-section view of the spinal fixation member of FIG. 7, taken along line B-B of FIG. 7.
Figure 9:
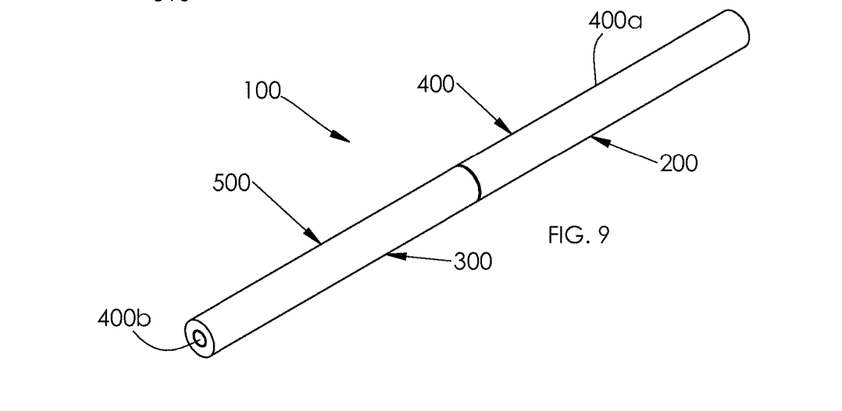
FIG. 9 is an isometric perspective view of the spinal fixation member of FIG. 7.

Referring now to FIGS. 7-9, a fixation member 100 is shown in accordance with another embodiment of the present disclosure. The fixation member 100 is defined by an elongated body 120 having a first end portion 200 and a second end portion 300 terminating at outermost ends 220 and 320, respectively. A core member 400 extends along the entire length of the elongated body 120 (see e.g., FIG. 8), and includes a first portion 400a and a second portion 400b. The first end portion 200 of the spinal fixation member 100 includes only the first portion 400a of the core member 400, and the second end portion 300 of the spinal fixation member 100 includes the second portion 400b of the core member 400 and an outer sheath member 500.

As shown in FIG. 8, the first portion 400a of the core member 400 has a uniform outer diameter or dimension 410 along the length of the first end portion 200 of the spinal fixation member 100. The second portion 400b of the core member 400 has a stepped or tapered profile through at least a portion of the second end portion 300 of the spinal fixation member 100, and is disposed within the outer sheath member 500.

The outer sheath member 500 has the same shape as that of the first portion 400a of the core member 400 such that the outer diameter or dimension 510 of the outer sheath member 500 matches the outer diameter or dimension 410 of the first portion 400a of the core member thereby providing the spinal fixation member 100 with a substantially uniform diameter along the length of the elongated body 120.

Similar to the spinal fixation member 10 of FIGS. 1-4, the length of the outer sheath member 500 may vary and may cover, in embodiments, up to half the length of the spinal fixation member 100, and the outer sheath member 500 is made from a less stiff material than the core member 400 such that the second end portion 300 of the fixation member 100 is less stiff than the first end portion 200 of the spinal fixation member 100. Also, the outer sheath member 500 may be disposed at both ends of the spinal fixation member 100, similar to the spinal fixation member 10' of FIGS. 5 and 6, to address cranial and caudal adjacent level failure.

Figure 10:
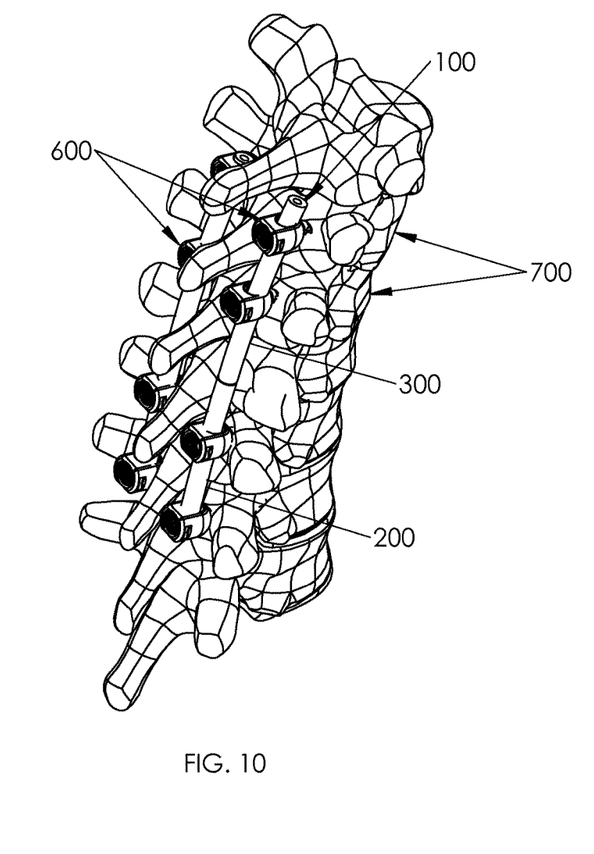
FIG. 10 is an in situ view of the spinal fixation member of FIG. 7.

FIG. 10 shows an in situ view of the spinal fixation member 100, whereby the spinal fixation member 100 is attached to pedicle screws 600. The pedicle screws 600 are anchored into vertebral bodies 700 of a spine. The spinal fixation member 100 is attached to the pedicle screws 600 such that the first and second end portions 200 and 300 are each positioned in respective pedicle screws 600. Pedicle screws 600 may be positioned at any desired position along the spinal fixation member 100. The second end portion 300 of spinal fixation member 100 has a reduced stiffness compared to the first end portion 200.

In use, a clinician may perform intradiscal work including, but not limited to, a discectomy and may supplement the disc space with various intradiscal implants including, but not limited to, an interbody implant. Next, the clinician utilizes posterior supplemental fixation in the form of bone anchor members 600 including, but not limited to, pedicle screws. The pedicle screws 600 are inserted into the vertebral bodies 700 adjacent to the intradiscal implant. Next, a spinal fixation member 10, 10', or 100 is inserted into the pedicle screws 600 and compression or distraction may be performed, as needed. The pedicle screws 600 are then locked, and the spinal fixation member 10, 10', or 100 is fixed in place. The spinal fixation member 10, 10', or 100 is locked into the pedicle screws 600.

In embodiments, spinal fixation member(s) may be provided in a kit. The kit is an assembled package with at least one core member and at least one sheath member. The core member may have any stiffness profile along the length thereof, and may include, for example, any of the core members 40, 40', and 400 described above. The kit may be provided with a plurality of core members having, for example, different diameters and/or shapes of the first portion of the core member, different tapering profiles at one or both ends of the core member, different lengths, and/or different materials from which they are made. The sheath member may have any stiffness profile along the length thereof, and may include, for example, any of the sheath members 50, 500 described above. The kit may include a plurality of sheath members having, for example, different diameters, shapes, and/or lengths, and/or different materials from which they are made. Accordingly, a clinician may pick and choose the core member(s) and the sheath member(s) necessary to form a spinal fixation member with the stiffness profile required of a surgical procedure.

A method of using the kit to assemble one or more spinal fixation members include taking a core member and affixing an outer sheath member to at least one end of the core member. The outer sheath member may be affixed by various well known means including, but not limited to, adhesion, overmolding, riveting, pinning, interference fit, press fit, or other such methods. Once assembled, the spinal fixation member may be inserted into vertebrae anchoring members, such as pedicle screws, hooks, cross connectors, staples, and the like. In embodiments, the spinal fixation member(s) may be implanted with the portion including the outer sheath member placed in a cranial vertebrae. The spinal fixation member(s) are fully reduced into place and the vertebrae anchoring members are locked to fix the spinal fixation member(s) in place.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A spinal rod for aligning vertebral bodies comprising:
    a core member including a first portion having a uniform outer diameter and a second portion extending from the first portion, at least a portion of the second portion having an outer diameter smaller than the uniform outer diameter of the first portion, the core member formed of a first material having a first modulus of elasticity; and
    a sheath member having a compound shape with an asymmetrical cross-sectional profile and including a lumen extending therethrough, the lumen sized for slidably receiving the second portion of the core member therein such that the sheath member is slidable relative to the core member and an outermost end of the second portion of the core member is disposed within the sheath member, the sheath member formed of a second material having a second modulus of elasticity different from the first modulus of elasticity.

2. The spinal rod according to claim 1, wherein the second portion of the core member is tapered.

3. The spinal rod according to claim 1, wherein the first and second portions of the core member are of equal lengths.

4. The spinal rod according to claim 1, wherein the first portion of the core member is cylindrical and has a circular-cross section.

5. The spinal rod according to claim 1, wherein the sheath member has an outer diameter that matches the uniform outer diameter of the first portion of the core member.

6. The spinal rod according to claim 1, wherein the sheath member includes an elongated body portion, an elongated head portion, and an elongated neck portion interconnecting the elongated body portion and the elongated head portion that define the asymmetrical cross-sectional profile.

7. The spinal rod according to claim 6, wherein the elongated body portion of the sheath member has an outer diameter that matches the uniform outer diameter of the first portion of the core member.

8. The spinal rod according to claim 1, wherein the first modulus of elasticity is higher than the second modulus of elasticity.

9. The spinal rod according to claim 1, wherein the core member is fabricated from a biocompatible metallic material and the sheath member is fabricated from a biocompatible polymeric material.

10. The spinal rod according to claim 1, wherein the core member includes a third portion extending from the first portion, at least a portion of the third portion having an outer diameter smaller than the uniform outer diameter of the first portion; and
    a second sheath member having a lumen extending therethrough, the lumen of the second sheath member sized for slidably receiving the third portion of the core member therein, the second sheath member formed of a third material having a third modulus of elasticity different from the first modulus of elasticity.

11. The spinal rod according to claim 10, wherein the first modulus of elasticity is higher than the third modulus of elasticity.

12. The spinal rod according to claim 1, wherein a length of the spinal rod varies in response to relative movement between the core member and the sheath member.

13. A kit for spinal surgery comprising:
    a core member having a first portion and a second portion, the first portion having a first outer diameter, and the second portion having a second outer diameter less than the first outer diameter;
    a first sheath member having a first lumen for slidably engaging the second portion of the core member; and
    a second sheath member having a second lumen for slidably engaging the second portion of the core member,
    wherein one of the first or second sheath members has an asymmetrical cross-sectional profile.

14. The kit according to claim 13, wherein the core member has a third portion opposite the second portion, the third portion having a third outer diameter less than the first outer diameter.

15. A method for aligning vertebral bodies comprising:
    inserting a first portion of a core member of a spinal rod into a first pedicle screw secured to a first vertebral body, the first portion of the core member having a uniform outer diameter, and the core member formed of a first material having a first modulus of elasticity; and
    inserting a sheath member having a second portion of the core member slidably disposed within a lumen of the sheath member with an outermost end of the second portion of the core member disposed within the sheath member, into a second pedicle screw secured to a second vertebral body, at least a portion of the second portion of the core member having an outer diameter smaller than the uniform outer diameter of the first portion of the core member, and the sheath member having a compound shape with an asymmetrical cross-sectional profile and formed of a second material having a second modulus of elasticity different from the first modulus of elasticity.

16. The method according to claim 15, further comprising anchoring the first and second pedicle screws into the first and second vertebral bodies prior to inserting the first portion of the core member into the first pedicle screw and inserting the sheath member into the second pedicle screw.

17. The method according to claim 16, wherein the first vertebral body is situated caudal to the second vertebral body, and wherein inserting a first portion of the core member into the first pedicle screw includes positioning the first portion of the core member in a caudal orientation relative to the second portion of the core member.

18. The method according to claim 16, wherein the first vertebral body is situated cranial to the second vertebral body, and wherein inserting a first portion of the core member into the first pedicle screw includes positioning the first portion of the core member in a cranial orientation relative to the second end portion of the core member.

* * * * *